United States Patent [19]

Hickmann

[11] 4,343,304

[45] Aug. 10, 1982

[54] VETERINARY INHALATION THERAPY APPARATUS

[76] Inventor: Horst R. Hickmann, 455 Montegor, Cincinnati, Ohio 45230

[21] Appl. No.: 169,740

[22] Filed: Jul. 17, 1980

[51] Int. Cl.[3] .............................................. A61M 11/00

[52] U.S. Cl. ................................ 128/200.14; 119/160; 119/15

[58] Field of Search ...................... 128/200.14, 200.18, 128/253, 205.26, 1 B,1 R, 203.25, 200.21, 200.22, 205.18; 119/15, 160; 248/124

[56] References Cited

U.S. PATENT DOCUMENTS

| | | | |
|---|---|---|---|
| 2,190,613 | 2/1940 | Sittler | 128/205.26 |
| 2,847,993 | 8/1958 | Woodruff | 128/200.21 |
| 3,091,343 | 5/1963 | Neumann | 248/124 |
| 3,097,645 | 7/1963 | Lester | 128/200.21 |
| 3,182,659 | 5/1965 | Blount | 128/200.21 |
| 3,353,536 | 11/1967 | Bird et al. | 128/200.18 |
| 3,379,194 | 4/1968 | Ziermann | 128/200.18 |
| 3,630,196 | 12/1971 | Bird | 128/200.18 |
| 3,826,255 | 7/1974 | Hanstad et al. | 128/200.18 |
| 3,878,570 | 4/1975 | Donnelly | 128/1 B |
| 3,941,092 | 3/1976 | Winters | 119/160 |
| 4,076,021 | 2/1978 | Thompson | 128/205.18 |
| 4,210,136 | 7/1980 | Apple | 128/204.21 |
| 4,244,361 | 1/1981 | Newbent | 128/205.25 |

OTHER PUBLICATIONS

Johnson et al., "Vaccination Against Pneumoencelphalitis (New Castle Disease) by Atomization in Incubators and Chick Boxes with the Bi Views", Vetinary Med., pp. 364–371, Sep. 1952.

*Primary Examiner*—Henry J. Recla
*Attorney, Agent, or Firm*—Frost & Jacobs

[57] ABSTRACT

A veterinary inhalation therapy apparatus for nebulizing the liquid medication used in the treatment of upper respiratory conditions in small animals, such as dogs and cats, confined in a cage or enclosure. The veterinary inhalation therapy apparatus comprises a portable electrically powered air compressor unit, a nebulizing assembly, flexible conduit connecting the air compressor and nebulizing assembly, and means for attaching the nebulizing assembly to a cage or enclosure. The air compressor unit produces a pressurized air flow which passes through the flexible conduit to the nebulizing means. In the nebulizing assembly the pressurized air flow interacts with liquid medication to produce a fine spray of the medication which is passed on into the cage or enclosure to effect inhalation therapy.

6 Claims, 4 Drawing Figures

VETERINARY INHALATION THERAPY APPARATUS

BACKGROUND OF THE INVENTION

1. Field Of The Invention.

The invention relates to a veterinary inhalation therapy apparatus and more particularly to a veterinary inhalation therapy apparatus using liquid medication reduced to a fine spray for the treatment of upper respiratory conditions in small animals such as dogs and cats, confined in a cage or enclosure.

2. Description Of The Prior Art.

The treatment of upper respiratory conditions in small animals (small animal is a description commonly used in the art to refer to a class of animals including most of the common pets, particularly dogs and cats) by the traditional oral and parenteral medication has proven unsatisfactory for many veterinary practitioners. The patients often do not accept this type of medication, causing the owners difficulty in giving it to their pets. These factors have increased the interest in using inhalation therapy as an alternative of treatment.

Inhalation therapy incorporating nebulized liquid medication is virtually unused in veterinary medicine, apparently due to a lack of veterinary literature on the subject and corresponding unavailability of equipment for veterinary use. Although nebulization is used to some extent in human medicine, its application is somewhat controversial and equipment developed for use with human patients is not practical for veterinary use. Nebulizing equipment developed for human medicine is expensive, cumbersome, and requires skilled technicians to operate and maintain it.

SUMMARY OF THE INVENTION

The veterinary inhalation therapy apparatus of the present invention is particularly adapted for application of nebulized liquid medication in treating upper respiratory conditions of small animals confined in a cage or enclosure. As used herein and in the claims, the phrase "liquid medication" is intended to describe liquid and liquid medication; including such components as water, a saline solution, various drugs, mucolytic detergents, proteolytic enzymes, and bronchodilating agents. The invention comprises a portable electrically powered air compressor, means for nebulizing liquid medication, a flexible conduit connecting the compressor and nebulizing means, and two distinct means for connecting the nebulizing means to a cage or enclosure. These elements combine in this invention to offer a veterinary inhalation therapy apparatus that is relatively inexpensive, easily portable, and can be conveniently operated and maintained by one not having a high level of skill or expertise in inhalation therapy.

DESCRIPTION OF THE PREFERRED EMBODIMENTS

Figure 1:
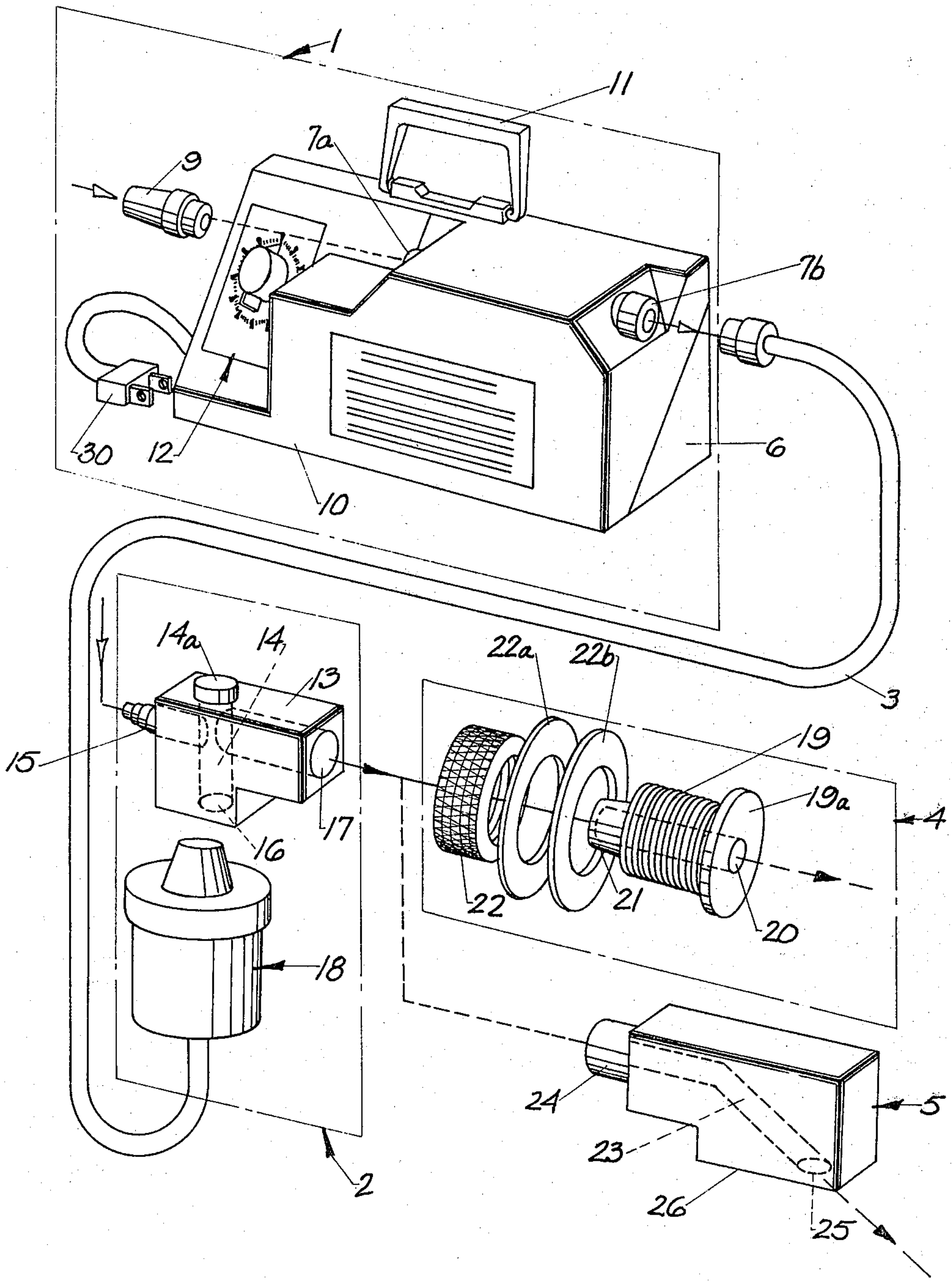
FIG. 1 is an exploded view of the veterinary inhalation therapy apparatus of the present invention.
Figure 2:
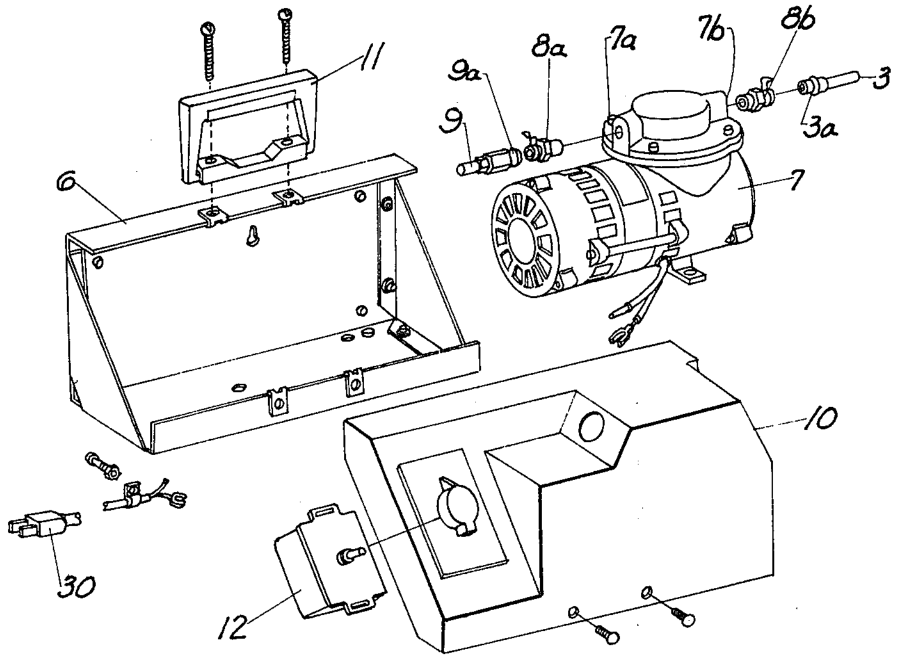
FIG. 2 is an exploded view of the portable electrically powered air compressor unit of the apparatus of the present invention.

The veterinary inhalation therapy apparatus of the present invention is shown in FIGS. 1 and 2 by exploded views. Included are a portable electrically powered air compressor unit generally indicated at 1, a nebulizing assembly 2, a flexible conduit 3, and alternate attaching means 4 and 5 for connecting the nebulizer means to a cage or enclosure.

The portable electrically powered compressor unit 1 (see FIG. 2) is composed of a supporting base 6; an electrically powered air compressor 7 attached to base 6 with an inlet 7*a* and outlet 7*b*; female quick connect fittings 8*a* and 8*b* therefor, and a conventional sintered or foam type filter element 9 which has a male quick connect fitting 9*a*. A shroud 10 is provided to surround the air compressor 7 and to be attached to the supporting base 6. A handle 11 facilitates portability of the apparatus; and a conventional timer control switch 12 initiates and regulates the duration of compressor operation.

The nebulizing assembly 2 comprises an adapting base 13 which has a filler passage 14 and cap 14*a* therefor, a serrated hose nipple 15, an inlet 16 and an outlet 17; and a nebulizing device 18.

The nebulizing device 18 is conventional and any appropriate nebulizer can be used. Excellent results have been achieved with a Hudson #1700 updraft nebulizer, manufactured by Hudson Oxygen Sales Company of Temecula, Calif. and Wadsworth, Ohio. This nebulizer coupled with the air compressor unit 1 can deliver an air flow of 15 l/min and has a aerosol generation of 0.3 cc/min. Up to 75% of the aerosol particles are less than 3 microns in diameter. This is desirable because investigators have indicated that smallness of the particles is a key to successful inhalation therapy.

Attaching means 4 enables connection of the inhalation therapy apparatus to a conventional cage and comprises threaded fitting 19 which has an axial bore 20. The fitting 19 terminates at one end in an unthreaded portion 19*a* of enlarged diameter and terminates at its other end in a tapered nose portion 21 adapted to be engaged in the outlet 17 of adapting base 13. The attaching means 4 also includes a removable cylindrical nut 22 and flat washers 22*a* and 22*b* which fit over the threads of fitting 19 and are sufficiently large in diameter to facilitate their use with a variety of cage bar spacings.

Figure 3:
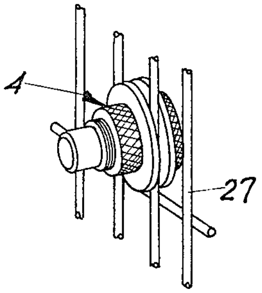
FIG. 3 is a fragmentary perspective view of vertical cage bars and the corresponding attaching means of the veterinary inhalation therapy apparatus.

The use of attaching means 4 is illustrated in FIG. 3. The washer 22*b* is placed on fitting 19 next to the unthreaded portion 19*a*. The fitting 19 is then passed between cage bars 27 until the bars contact the washer 22*b*; the unthreaded portion 19*a* being on the inside of the bars 27. The other washer 22*a* is then placed on fitting 19 until it contacts bars 27 from the outside. The nut 22 is then threaded on fitting 19 and tightened, securely fastening attaching means 4 to the cage bars 27. The nebulizing assembly 2 would then be connected to attaching means 4 and a covering (not shown), such as plastic sheeting, placed over the cage door to better contain the spray of liquid medication.

FIG. 1 also illustrates an alternate attaching means 5 for connecting the inhalation therapy apparatus to a chamber type enclosure, such as a 10 gallon aquarium or the like. Attaching means 5 has an internal passage 23 through its body. The passage 23 terminates at one end in a tapered nose portion 24 adapted to be received in outlet 17 of adapting base 13 and terminates at the other end in an outlet 25 at the body's lower surface 26.

Figure 4:
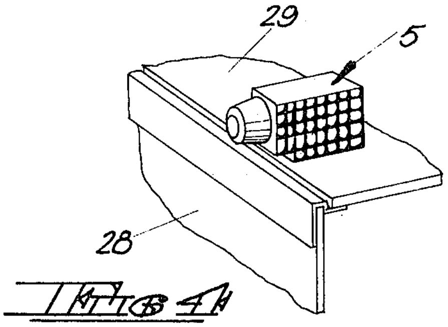
FIG. 4 is a fragmentary perspective view of the upper horizontal surface of a chamber-type enclosure and the corresponding attaching means of the veterinary inhalation therapy apparatus.

FIG. 4 illustrates attaching means 5 as used with a chamber type enclosure 28, such as an aquarium, having a lid 29 or other appropriate covering. The lid 29 has an opening therein for alignment with the outlet 25 in means 5. For rigidly attaching means 5 to the lid 29 means (not shown), such as locating pins and screws in bottom surface 26, are used as required.

The apparatus is set up by first removing filler cap 14*a* in adapting base 13, adding the liquid medication through the filter passage 14, and replacing filter cap 14*a*. The medication passes on through adapting base 13 into the nebulizing device 18. The entire nebulizing assembly 2 is then connected to attaching means 4 or attaching means 5 depending on the type of enclosure used, as shown in FIGS. 3 and 4. Also, if input of additional gas, such as oxygen, is desired, it is connected to and input through hose nipple 15 of adapting base 13; if not, hose nipple 15 is capped. Finally, the compressor unit 1 is connected to a source of electrical energy by means of plug 30.

Operation of the veterinary inhalation therapy apparatus begins with activating the portable electrically powered air compressor unit 1 by means of timer control switch 12 and setting the desired duration thereon. The air compressor 7 begins to run causing an intake of ambient air through filter element 9 and compressor inlet 7*a*, and producing an output of a pressurized air flow through outlet 7*b* into the flexible conduit 3 which is connected to the compressor unit 1 by male quick connect 3*a*. The air flow continues through conduit 3 passing into the nebulizing device 18 where the air flow interacts with the liquid medication contained therein, reducing the medication to a fine spray. This spray of medication passes from the nebulizing device 18 through the inlet 16 of adapting base 13 where it mixes with any additional gas input (via hose nipple 15, if used) and goes on through outlet 17 into either attaching means 4 or 5 as previously described, passing finally into the cage or enclosure.

Modifications may be made in the veterinary inhalation therapy apparatus of the present invention without departing from its spirit or purpose.

I claim:

1. A veterinary inhalation therapy apparatus by which liquid medication is reduced to a fine spray for the treatment of upper respiratory conditions in a small animal confined in a cage of the type having bars in a vertical plane with a spaced parallel relationship, said apparatus comprising:

(a) a portable electrically powered air compressor unit for producing a pressurized air output;

(b) a flexible conduit having inlet and outlet ends, the inlet end being connected to and receiving the output of said compressor unit;

(c) a nebulizing assembly having an inlet connected to the outlet end of said flexible conduit and an outlet, said nebulizing assembly including a reservoir for the liquid medication used in said inhalation therapy and means for reducing the medication in said reservoir to a fine spray by the interaction with the pressurized air flow from said compressor; and (d) means for delivering said spray from said outlet of said nebulizing assembly to said cage, said means comprising:

(1) a straight, tubular fitting having an inlet end connected to said outlet of said nebulizing assembly and an outlet end of enlarged diameter adapted to be located within said cage, said fitting being externally threaded from said inlet end to said outlet end; and (2) a nut threadedly engaged on said fitting whereby said fitting can be located between an adjacent pair of said bars with said last mentioned bars being clamped between said nut and said enlarged outlet end of said fitting.

2. A veterinary inhalation therapy apparatus by which liquid medication is reduced to a fine spray for the treatment of upper respiratory conditions in a small animal confined in an enclosure having a horizontal top, said apparatus comprising:

(a) a portable, electrically powered air compressor unit for producing a pressurized air output;

(b) a flexible conduit having inlet and outlet ends, the inlet end being connected to and receiving the output of said compressor unit;

(c) a nebulizing assembly having an inlet connected to the outlet end of said flexible conduit and an outlet, said nebulizing assembly including a reservoir for the liquid medication used in said inhalation therapy and means for reducing the medication in said reservoir to a fine spray by the interaction with the pressurized air flow from said compressor; and (d) means for delivering said spray from said outlet of said nebulizing assembly to said cage, said means comprising:

(1) a fitting in the shape of a rectangular solid having a bottom surface, said fitting having an internal passage terminating at one end in an inlet opening connected to said outlet of said nebulizing assembly and terminating at its other end in an outlet opening in said bottom surface of said fitting; and (2) means for rigidly attaching said fitting to said horizontal top of said enclosure, said horizontal top having an inlet opening therethrough, said outlet of said fitting being in alignment with said inlet opening in said enclosure top.

3. The apparatus claimed in claim 1 or 2 wherein said portable electrically powered air compressor unit comprises:

(a) a supporting base;

(b) an electrically powered air compressor affixed to said base and having an inlet for ambient air and an outlet for said air under pressure;

(c) a filter element connected to said compressor inlet;

(d) a shroud surrounding said air compressor, said shroud being attached to said base and having a handle whereby the compressor unit is made portable; and (e) a timer control switch operatively connected to said electrically powered air compressor for initiating and regulating the duration of the flow of electricity to said compressor, whereby the pressurized air flow from said compressor is correspondingly controlled.

4. The apparatus claimed in claim 1 or 2 wherein said nebulizing assembly comprises:

(a) an adapting base having a passage therethrough terminating in inlet and outlet openings;

(b) a nebulizing device providing a reservoir for said liquid medication and having an inlet for connection to said outlet end of said flexible conduit and an outlet connected to said adapting base inlet opening whereby a pressurized air flow from said compressor unit entering through said nebulizing device inlet causes the liquid medication contained therein to be reduced to a fine spray; and (c) a filler opening connected to said passage through which said liquid medication is introduced into said nebulizing device and a cap for said filler opening.

5. The apparatus claimed in claim 4 including an additional inlet to said adapting base passage through which a gas can be added to said fine spray of liquid medication.

6. The apparatus claimed in claim 1 including a pair of washers mounted on said fitting between said enlarged outlet end thereof and said nut, said washers being positionable one to each side of said adjacent cage bars, said adjacent cage bars being clamped by said washers, said washers being in abutment with said nut and said enlarged outlet end of said fitting respectively.

* * * * *